United States Patent [19]

Takei et al.

[11] 4,320,139

[45] Mar. 16, 1982

[54] METHOD OF ENHANCING THE ACTIVITY OF FAST EVAPORATING INSECTICIDES

[75] Inventors: Yasuharu Takei; Yasuharu Kodama; Hiroshi Shimoda; Satoshi Ohi, all of Hiroshima, Japan

[73] Assignee: Fumakilla Limited, Tokyo, Japan

[21] Appl. No.: 119,765

[22] Filed: Feb. 8, 1980

Related U.S. Application Data

[63] Continuation of Ser. No. 927,033, Jul. 24, 1978, abandoned.

[30] Foreign Application Priority Data

Aug. 5, 1977 [JP] Japan ................... 52-093373

[51] Int. Cl.³ .............. A01N 37/00; A01N 37/08; A01N 43/16

[52] U.S. Cl. .................... 424/282; 424/40; 424/189; 424/305; 424/306

[58] Field of Search ............... 424/40, 189, 282, 306, 424/305

[56] References Cited

U.S. PATENT DOCUMENTS

| | | | |
|---|---|---|---|
| 1,957,429 | 5/1934 | Adams | 424/189 |
| 2,369,429 | 2/1945 | Boissonou | 424/189 |
| 2,428,494 | 10/1947 | Jones et al. | 424/189 |
| 2,664,382 | 12/1953 | Omohundro et al. | 424/189 |
| 3,560,613 | 2/1971 | Miskus et al. | 424/189 |
| 3,669,989 | 6/1972 | Itaya et al. | 424/282 |
| 3,723,615 | 3/1973 | Okuno | 424/306 |
| 3,766,218 | 10/1973 | Ueda et al. | 424/306 |
| 3,795,696 | 3/1974 | Katsuda et al. | 424/306 |
| 3,819,823 | 6/1974 | Okuno | 424/306 |
| 3,839,562 | 10/1974 | Chodnekar et al. | 424/282 |
| 3,849,571 | 11/1974 | Bordencu et al. | 424/282 |

FOREIGN PATENT DOCUMENTS 41-11997  6/1966  Japan ....................... 424/189

OTHER PUBLICATIONS

King; Chemicals Evaluated as Insecticides and Repellents at Orlando, Fla., May 1954, pp. 1-18, 21, 44, 45, 120, 145, 148, 156, 220, 232, 248, 268, 269, 309, 311 & 395-397.

*Primary Examiner*—Allen J. Robinson
*Attorney, Agent, or Firm*—Pearne, Gordon, Sessions, McCoy & Granger

[57] ABSTRACT

A method of enhancing the activity of a fast evaporating insecticide characterized by incorporating in a pyrethroid insecticide one or more compounds selected from the group consisting of a phthalic ester, aliphatic ester, aliphatic dibasic ester, aromatic carboxylic ester, higher aliphatic alcohol, polyhydric alcohol, glycol ether and a hydrocarbon having 10 or more carbon atoms and one or more antioxidants.

1 Claim, No Drawings

METHOD OF ENHANCING THE ACTIVITY OF FAST EVAPORATING INSECTICIDES

This is a continuation, of application Ser. No. 927,033, filed July 24, 1978, now abandoned.

BACKGROUND OF THE INVENTION (1) Field of the Invention:

This invention relates to a method of enhancing the activity of a fast evaporating insecticide, and more particularly, to a method of enhancing the activity of an evaporating insecticide that rapidly evaporates the active ingredient, characterized by incorporating in a pyrethroid insecticide one or more compounds selected from the group consisting of a phthalic ester, aliphatic ester, aliphatic dibasic ester, aromatic carboxylic ester, higher aliphatic alcohol, polyhydric alcohol, glycol ether and a hydrocarbon having 10 or more carbon atoms and one or more antioxidants.

(2) Description of the Prior Art:

A fumigating insecticide is known as a conventional insecticide that evaporates the active ingredient upon short heating. Comprising an active ingredient and a combustible base that carries it, the fumigating insecticide evaporates the active ingredient using the heat of combustion produced by combustion of the combustible base. Examples of the commonly employed active ingredient are an organophosphrous insecticide, a pyrethroid insecticide, etc. The optimal temperature at which these active ingredients evaporate differs from one kind to another. However, according to this method that utilizes the heat of combustion of the combustible base, temperature control is so difficult to achieve that combustion easily results in an excessively high temperature, where as much as about 60 to 70% of the active ingredient decomposes thermally.

To eliminate such defect of the conventional method of killing insects using fast evaporating insecticides, the present inventors have conducted various studies on the effective evaporation upon short heating of a pyrethroid insecticide and its insecticidal effect, and found that by incorporating in a pyrethroid insecticide at least one compound selected from the group consisting of a phthalic ester, aliphatic ester, aliphatic dibasic ester, aromatic carboxylic ester, higher aliphatic alcohol, polyhydric alcohol, glycol ether, a hydrocarbon having 10 or more carbon atoms and an antioxidant and by evaporating the active ingredient using a heating element having an evaporating temperature suitable for the active ingredient used, a high degree of evaporation of the active ingredient can be provided and with a relatively small degree of its heat decomposition. However, we have also found that if at least one antioxidant or at least one compound other than antioxidant is independently incorporated into a pyrethroid insecticide, the degree of evaporation of the active ingredient is increased but no enhancement in the insecticidal effect is obtained.

The present inventors therefore continued their research to eliminate this defect and have finally completed the present invention which will be described hereinafter.

SUMMARY OF THE INVENTION

The method according to this invention of enhancing the activity of a fast evaporating insecticide is therefore characterized by incorporating in a pyrethroid insecticide one or more compounds selected from the group consisting of a phthalic ester, aliphatic ester, aliphatic dibasic ester, aromatic carboxylic ester, higher aliphatic alcohol, polyhydric alcohol, glycol ether and a hydrocarbon having 10 or more carbon atoms as well as one or more antioxidants. According to the method of this invention, not only is the degree of evaporation of the active ingredient increased but also the activity of the insecticide is enhanced to provide rapid and effective killing of insects.

In this connection, agents that have been conventionally used for enhancing the activity of pyrethroid insecticides that incorporate them include piperonyl butoxide, syneprin 500, octachlorodipropyl ether, etc., but none of them have been used in a fast evaporating insecticide.

Surprisingly enough, we have found that no enhancement of insecticidal activity is obtained if the compounds and antioxidants to be used in the method of this invention are incorporated into a pyrethroid insecticide in general types of preparation, such as aerosol, oil-borne insecticide, emulsible insecticide, etc., and that therefore these compounds or antioxidants are not agents that are capable of enhancing the activity of pyrethroid insecticides in general but are only effective if at least one of the compounds as well as at least one of the antioxidants are incorporated into a pyrethroid insecticide for use as a fast evaporating insecticide. The most plausible explanation of this phenomenon would be the synergism of the compounds and antioxidants as provided by a heating medium.

DETAILED DESCRIPTION OF THE INVENTION

Following are the compounds which are considered particularly practical of the compounds and antioxidants which are suitable for use in the method of this invention. Their numbers below are keyed to the numbers given in Table 1, 2, and 3 of Examples 1, 2 and 3 set forth hereinafter.

Phthalic esters:
(1) Di-2-ethylhexyl phthalate
(2) Di-isodecyl phthalate
(3) Dilauryl phthalate
(4) Dibenzyl phthalate Aliphatic Esters:
(5) Butyl oleate
(6) Butyl stearate
(7) Isopropyl mirystate Aliphatic dibasic esters:
(8) Tributyl citrate
(9) Dibutyl maleate
(10) Acetylbutyl citrate
(11) Di-2-ethylhexyl adipate
(12) Diisodecyl adipate
(13) Di-2-ethylhexyl sebacate
(14) Dibenzyl sebacate
(15) Diiso-octyl sebacate
(16) Tributyl citrate Aromatic carboxylic esters:
(17) Triiso-octyl trimellitate
(18) Butylphthalylbutyl glycolate Higher aliphatic alcohols:
(19) Oleyl alcohol
(20) Lauryl alcohol Polyhydric alcohols:
(21) Diethylene glycol
(22) Dipropylene glycol Glycol ether:
(23) Diethylene glycol monobutyl ether
Hydrocarbons:
(24) Polybutene
(25) Dipentene
Antioxidants:
(1) Dibutylhydroxy toluene (BHT)
(2) Butylhydroxy anisole (BHA)
(3) n-propyl gallate
(4) Tocopherol
(5) Octadecyl-3-(3,5-ditertiarybutyl-4-hydroxyphenyl) propionate
(6) Pentaerythtyl-tetrakis [3-(3,5-ditertiarybutyl-4-hydroxyphenyl)propionate]
(7) 2,5-ditertiarybutyl hydroquinone
(8) 4,4'-thiobis(3-methyl-6-tertiarybutyl phenol)
(9) 2,2'-methylene-bis-(4-methyl-6-tertiarybutyl phenol)

Other effective compounds are dimethyl phthalate, diethyl phthalate, dibutyl phthalate, etc. as the phthalic ester; methyl oleate, methyl myristate, etc. as the aliphatic ester; methyl benzoate, ethyl benzoate, 2-ethylhexyl hydroxy benzoate, etc. as the aromatic carboxylic ester; hexyl alcohol, octyl alcohol, cetyl alcohol, stearyl alcohol, etc. as the higher aliphatic alcohol; glycerin, 1,4-butane diol, 1,5-pentane diol, dl-2,5-hexane diol, etc. as the polyhydric alcohol; diethylene glycol monomethyl ether, diethylene glycol monoethyl ether, diethylene glycol diethyl ether, etc. as the glycol ether; undecane, decane, octadecane, phenanthrene, eicosane, p-diethyl benzene, m-divinyl benzene, ethyl naphthalene, dimethyl naphthalene, p-ethyl toluene, 1,1-diphenyl ethane, dimethyl biphenyl, polypropylene, etc. as the hydrocarbon having 10 or more carbon atoms. Since the method of this invention evaporates the active ingredient by heating a heating element to a temperature in the range of from 150° to 400° C., the above compounds preferably have a boiling temperature of 150° C. or higher, and most preferably, they have a boiling temperature in the range of from 200° to 300° C. Those compounds which have a boiling temperature lower than 150° C. cannot advantageously be used in the method of this invention. The above mentioned hydrocarbons that have 10 or more carbon atoms can therefore be effectively used because they usually have a boiling temperature of 150° C. or higher.

According to the method of this invention, one or more compounds as well as one or more of the antioxidants described above are incorporated into a pyrethroid insecticide, and the resulting composition is used either by impregnating a porous carrier such as a pulp sheet, glass fibers, etc. with it or it is formed into various types of preparation such as paste, cream or granules. A separately prepared heating element is then heated at 150° to 400° C. for a period that generally ranges from several minutes to several tens of minutes to thereby evaporate the active ingredient from the insecticidal preparation. The heating element available for use herein is for example a resistive heating element, a semiconductive element, self-burning gas or carbon, a burning agent, or a compound which produces heat by absorption of moisture or oxygen. If the additive compound defined above is used in an amount ranging from the equivalent to several times the active ingredient and the antioxidant also defined above is used in an amount of from about 5 to 10% of the active ingredient, the effect obtained is practically satisfactory, but this invention is by no means limited to these ranges.

Examples of the suitable pyrethroid insecticide that can be used in the method of this invention are 3-allyl-2-methylcyclopenta-2-en-4-on-1-yl dl-cis,trans-chrysanthemate (hereunder referred to as allethrin), 3-allyl-2-methylcyclopenta-2-en-4-on-1-yl d-cis,trans-chrysanthemate (hereunder referred to as d-cis,trans-allethrin), d-3-allyl-2-methyl-cyclopenta-2-en-4-on-1-yl d-trans-chrysanthemate (hereunder referred to as d,d-allethrin), 3-phenoxybenzyl-d-cis,trans-chrysanthemate (hereunder referred to as phenothrin), 3-phenoxybenzyl-dl-cis,trans-3-(2,2-dichlorovinyl)-2,2-dimethyl-1-dichloropropane carboxylate (hereunder referred to as permethrin), 5-benzyl-3-furylmethyl-dl-cis,trans-chrysanthemate (hereunder referred to as resmethrin), etc.

The effect that can be achieved by the method of this invention is now described in greater detail by the following examples, but it should be understood that this invention is by no means limited by these examples.

EXAMPLE 1

A plurality of insecticidal mats were prepared by impregnating pulp sheets each having an area of 50 cm$^2$ and a thickness of 0.75 mm with a pyrethroid insecticide, an additive compound and an antioxidant. Table 1 shows the results of the following tests on these mats.

TEST ON INSECTICIDAL ACTIVITY

Butter traps each containing 10 Blattella germanica Linné in a laboratory dish having an inner diameter of 9 cm and a height of 6 cm were placed in the four corners of a 6-mat room (approx. 9.72 m$^2$ wide). Each of the above prepared insecticidal mats were placed in the center of the room and heated with a heating element for 30 minutes. The knockdown time (KT-50) and the fatality (Kill) after 24 hours were determined.

EVAPORATION TEST

The degree of evaporation of the active ingredient was measured by heating each insecticidal mat with the heating element for 30 minutes.

TABLE 1

| | Content (mg) | Number of Compound | Content (mg) | Number of Antioxidant | Content (mg) | Evaporating temp. (°C.) | KT-50 (min) | Kill (%) | Evaporation degree (%) |
|---|---|---|---|---|---|---|---|---|---|
| Allethrin | 1000 | 5 | 1000 | 1 | 50 | 230–250 | 18.48 | 97.3 | 95.7 |
|  | 1000 | 1 |  |  |  |  | 17.51 | 95.6 | 93.6 |
| d-cis, trans-allethrin | 500 | 6 | 500 | 5 | 25 | 230–250 | 16.20 | 100.0 | 92.5 |
|  | 500 | 3 |  |  |  |  | 15.55 | 98.5 | 93.9 |
| d,d-trans-allethrin | 250 | 9 | 250 | 6 | 15 | 230–250 | 12.46 | 100.0 | 94.6 |
|  | 250 | 24 |  |  |  |  | 13.31 | 100.0 | 95.2 |
| Permethrin | 250 | 7 | 500 | 3 | 50 | 250–270 | 30< | 100.0 | 97.8 |
|  | 250 | 21 |  |  |  |  | 30< | 100.0 | 99.2 |
| Phenothrin | 500 | 16 | 500 | 4 | 50 | 270–300 | 30< | 93.7 | 96.3 |
|  | 500 | 20 |  |  |  |  | 30< | 95.3 | 94.5 |
| Resmethrin | 500 | 8 | 500 | 7 | 25 | 250–270 | 19.51 | 100.0 | 91.3 |
|  | 500 | 12 |  |  |  |  | 20.30 | 98.5 | 90.6 |

TABLE 1-continued

|  | Content (mg) | Number of Compound | Content (mg) | Number of Antioxidant | Content (mg) | Evaporating temp. (°C.) | KT-50 (min) | Kill (%) | Evaporation degree (%) |
| --- | --- | --- | --- | --- | --- | --- | --- | --- | --- |
| Permethrin | 125 | 22 | — | — | — |  | 23.10 | 100.0 | 98.6 |
| d-cis, trans-allethrin | 250 | 15 | 400 | 3 | 20 | 250–270 | 23.05 | 100.0 | 96.7 |
| Permethrin | 125 | 6 | — | — | — |  | 22.51 | 100.0 | 95.8 |
| d,d-trans-allethrin | 125 | 7 | 250 | 7 | 25 | 250–270 | 22.48 | 100.0 | 98.2 |
| Phenothrin | 250 | 13 | — | — | — |  | 22.54 | 95.6 | 95.6 |
| d-cis, trans-allethrin | 250 | 19 | 500 | 2 | 50 | 270–300 | 24.35 | 93.8 | 95.5 |
| Phenothrin | 250 | 23 | — | — | — |  | 25.30 | 100.0 | 94.3 |
| d,d-trans-allethrin | 125 | 21 | 400 | 8 | 40 | 270–300 | 24.56 | 95.8 | 96.8 |
| Resmethrin | 250 | 14 | — | — | — |  | 17.31 | 100.0 | 91.2 |
| d-cis, trans-allethrin | 250 | 2 | 500 | 9 | 50 | 250–270 | 18.05 | 98.3 | 92.5 |
| Allethrin | 1000 | — | — | — | — | 230–250 | 25.60 | 40.5 | 56.4 |
| d,d-cis,trans-allethrin | 500 | — | — | — | — | 230–250 | 23.30 | 50.1 | 55.3 |
| d,d-trans-allethrin | 250 | — | — | — | — | 230–250 | 20.35 | 65.5 | 57.6 |
| Permmethrin | 250 | — | — | — | — | 250–270 | 30> | 52.3 | 43.2 |
| Phenothrin | 500 | — | — | — | — | 270–300 | 30> | 35.0 | 36.7 |
| Resmethrin | 500 | — | — | — | — | 250–270 | 30> | 38.3 | 43.6 |

EXAMPLE 2

Eight kinds of insecticidal mats were prepared by impregnating a pulp sheet having an area of 50 cm² and a thickness of 0.5 mm with 500 mg of d-cis,trans-allethrin or 250 mg of d,d-trans-allethrin, 500 mg of an additive compound, and 10% of an antioxidant as set forth in Table 2. Two commercially available preparations comprising 1000 mg of permethrin and 1500 mg of 0,0-dimethyl-0-2,2-dichlorouinyl phosphate, respectively, were used as the controls. Table 2 shows the results of the tests on insecticidal activity and evaporation that were run in the same manner as used in Example 1.

TABLE 2

|  | Number of Compound | Anti-oxidant | KT-50 | Kill (%) | Evaporation degree (%) |
| --- | --- | --- | --- | --- | --- |
| d-cis, trans-allethrin | — | — | 29.39 | 50 | 52.3 |
|  | 7 | — | 27.05 | 69 | 90.2 |
|  | — | 5 | 26.35 | 65 | 91.6 |
|  | 7 | 5 | 15.31 | 100 | 98.2 |
| d,d-trans-allethrin | — | — | 22.45 | 60 | 48.3 |
|  | 24 | — | 20.37 | 75 | 90.5 |
|  | — | 6 | 21.05 | 70 | 92.3 |
|  | 24 | 6 | 12.35 | 100 | 97.6 |
| 1000 mg of permethrin as a fumigating insecticide |  |  | 38.55 | 100 | 36.8 |
| 1500 mg of 0,0,dimethyl-0-2,2-dichlorovinyl phosphate as a fumigating insecticide |  |  | 39.49 | 100 | 21.3 |

EXAMPLE 3

Six insecticidal mats were prepared by impregnating a pulp sheet having an area of 50 cm² and a thickness of 0.75 mm with 500 mg of d-cis,trans-allethrin; two of the mats were impregnated with 250 mg each of two additive compounds and 5% each of antioxidants, and the remaining four mats impregnated with only two kinds of additive compound or antioxidant, as set forth in Table 3. Table 3 also shows the results of the tests on insecticidal activity and evaporation that were performed in the same manner as used in Example 1.

TABLE 3

| Number of Compound | Number of Antioxidant | KT-50 (min) | Kill(%) | Evaporation degree (%) |
| --- | --- | --- | --- | --- |
| 10 | 24 | 1 | 3 | 14.47 | 100 | 96.3 |
| 10 | 24 | — | — | 27.53 | 79 | 88.6 |
| — | — | 1 | 3 | 25.31 | 73 | 90.5 |
| 6 | 14 | 4 | 7 | 15.05 | 100 | 92.3 |
| 6 | 14 | — | — | 27.31 | 78 | 85.6 |
| — | — | 4 | 7 | 29.11 | 70 | 91.0 |

We claim:

1. A method for combating insects which comprises applying a fast evaporating insecticide to insects in an insecticidally effective amount, by evaporating said insecticide, by rapid heating of the said insecticide to a temperature between 150° C. and 400° C., said insecticide comprising a pyrethroid insecticide selected from the group consisting of allethrin, d-cis, trans-allethrin, d,d-allethrin, phenothrin, permethrin or resmethrin, at least one evaporation additive compound selected from the group consisting of dimethyl phthalate, diethyl phthalate, dibutyl phthalate, di-2-ethylhexyl phthalate, diisodecyl phthalate, dilauryl phthalate, dibenzyl phthalate, butyl oleate, butyl stearate, methyl myristate, isopropyl myristate, tributyl citrate, dibutyl maleate, acetylbutyl citrate, di-2- ethylhexyl adipate, diisodecyl adipate, di-2-ethylhexyl sebacate, dibenzyl sebacate, diiso-octyl sebacate, triiso-octyl trimellitate, butylphthalylbutyl glycolate, oleyl alcohol, lauryl alcohol, diethylene glycol, dipropylene glycol, diethylene glycol monobutyl ether, decane, undecane, and dipentene, and being present in an amount ranging from about 100% to about 320% by weight of said pyrethroid insecticide, and at least one antioxidant selected from the group consisting of dibutyl-hydroxy toluene, butylhydroxy anisole, n-propyl gallate, tocopherol, octadecyl-3- (3,5-ditertiarybutyl-4-hydroxyphenyl) propionate, pentaerythtyltetrakis [3-(3,5-ditertiarybutyl-4-hydroxyphenyl)propionate], 2,5-ditertiarybutyl hydroquinone, 4,4'-thiobis(3-methyl-6-tertiarybutyl phenol), and 2,2'-methylene-bis-(4-methyl-6-tertiarybutyl phenol), said antioxidant being present in an amount ranging from about 5% to about 10% by weight of said pyrethroid insecticide.

* * * * *